(12) United States Patent
Grasha et al.

(10) Patent No.: US 7,612,027 B2
(45) Date of Patent: *Nov. 3, 2009

(54) HAND CLEANSING FORMULATION

(75) Inventors: Pierre Bruno Grasha, Cormontreuil (FR); Neil Paul Joyce, Paris (FR)

(73) Assignee: Deb IP Limited, Belper, Derbyshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/081,177

(22) Filed: Apr. 11, 2008

(65) Prior Publication Data

US 2008/0227677 A1 Sep. 18, 2008

Related U.S. Application Data

(62) Division of application No. 10/514,106, filed as application No. PCT/IB03/01683 on Apr. 30, 2003, now Pat. No. 7,410,937.

(30) Foreign Application Priority Data

May 13, 2002 (FR) .................................. 02 05878

(51) Int. Cl.
*A61K 7/00* (2006.01)
(52) U.S. Cl. ..................... 510/130; 510/137; 510/138; 510/139; 510/462; 510/477
(58) Field of Classification Search ........................ None
See application file for complete search history.

(56) References Cited

U.S. PATENT DOCUMENTS

| | | | |
|---|---|---|---|
| 4,738,987 A | 4/1988 | Mattson et al. | ............. 514/770 |
| 5,877,133 A | 3/1999 | Good | |
| 6,191,087 B1 | 2/2001 | Henneberry et al. | |
| 6,235,698 B1 | 5/2001 | Vlasblom | |
| 6,376,438 B1 | 4/2002 | Bruecher et al. | |
| 6,432,429 B1 | 8/2002 | Maddern et al. | ............. 424/402 |
| 6,494,920 B1 | 12/2002 | Weuthen et al. | ................. 8/137 |
| 6,635,702 B1 | 10/2003 | Schmucker-Castner et al. | ........................... 524/291 |
| 2002/0010114 A1 | 1/2002 | Dufay et al. | ................. 510/130 |
| 2002/0039561 A1 | 4/2002 | Doughty et al. | ............... 424/59 |

FOREIGN PATENT DOCUMENTS

| | | |
|---|---|---|
| DE | 42 40 160 | 6/1994 |
| GB | 1 396 730 | 6/1975 |
| WO | WO 03 026609 | 4/2003 |

*Primary Examiner*—Necholus Ogden, Jr.
(74) *Attorney, Agent, or Firm*—Dowell & Dowell P.C.; Lynn C. Schumacher

(57) ABSTRACT

This invention provides heavy-duty cleansers (HDHC), with a high level of biodegradability and little or no ecotoxicity, with a high level of efficiency and a maximum skin tolerance and no systemic toxicity. In the broadest aspect of the invention there is provided a cleansing formulation comprising 5 to 10% of one or more methylesters of vegetable saturated and/or unsaturated fatty acids which may be from several natural sources including sunflower seed oil, soybean oil, rape seed oil, or coconut oil. The formulation includes between about 10% to 30% of one or more surfactants and a preferred combination of surfactants includes at least one ethoxylated fatty alcohol, one alkyl polyoxyethylene glycol, one alkanolamide and one polymeric quaternary ammonium salt.

16 Claims, No Drawings

HAND CLEANSING FORMULATION

CROSS REFERENCE TO RELATED PATENT APPLICATIONS

This patent application is a Divisional application of U.S. patent application Ser. No. 10/514,106 entitled HAND CLEANSING FORMULATION filed on Nov. 12, 2004 in the name of the same inventors, which has now been allowed, which is a National Phase application claiming the benefit of PCT/IB03/01683 filed on May 13, 2003; which further claims priority benefit of French Patent Application No. 0205878, filed on May 13, 2002, entitled HAND CLEANSING FORMULATION, all of which are incorporated herein by reference in their entirety.

FIELD OF THE INVENTION

This invention relates generally to heavy-duty cleansers (HDHC), with or without solvent, with a high level of biodegradability and little or no ecotoxicity, with a high level of efficiency and a maximum skin tolerance and no systemic toxicity.

BACKGROUND OF THE INVENTION

There are two major categories of heavy duty hand cleansers (HDHC) currently on the market. The first include formulations without solvent and with or without scrubbing microparticles, typically derived from vegetable, mineral or organic origins. These products contain some surfactants which act by emulsifying greasy stains. These scrubbing micro-particles provide a mechanical effect during the hand washing and, thus, increase the cleansing power of the preparation.

The second category of so called heavy duty cleansers include formulations with solvents present, with or without scrubbing particles, with surfactants (soap and/or synthetic and/or semi-synthetic surfactants). These cleansers containing solvents combine the emulsifying properties of the surfactants with the solubilizing properties of the solvent. The presence of micro-particles will increase the cleansing power of these formulations as in the case of non-solvented formulations. The solvents are generally hydrocarbon solvents without any aromatics (or trace amounts present only) and used at an average concentration of 10 to 30%. Terpenes such as d-limonene are also often used at a concentration of 1 to 10%. Hydrophilic solvents such as propylenic glycol ethers are rarely used. Solvents are often criticized for their defatting properties on skin which may induce irritation.

D-limonene has an aesthetic advantage of having a very pleasant orange aroma while functionally it is very effective on grease, but a drawback to this solvent is the fact that, in its pure form, it is flammable and is considered harmful to the environment. In addition, some allergies to oxidized terpenes are described in scientific literature. This is why d-limonene for example is systematically protected from oxidation using a cosmetic anti-oxidant (in most cases the anti-oxidants used are Butyl-Hydroxy-Anisol (BHA) and/or Butyl-Hydroxy-Toluene (BHT) which also have a sensitizing potential). Hydrocarbon and terpene-based solvents have a low biodegradability potential and are known for having a significant ecotoxicity on aquatic life.

The use of surfactants only to obtain a high level of cleansing efficiency is possible but needs a high concentration of active matter which is costly and not suitable in terms of the environment. It would be very advantageous to provide a cleanser having a combination of solvent, surfactant(s) and scrubbing microparticles would allow one to reduce the total quantity of active matter in the finished product.

SUMMARY OF THE INVENTION

In one aspect of the invention there is provided a skin cleansing formulations, comprising
a) between about 5% to about 10% by weight of at least one of a methylester of a saturated or unsaturated fatty acid;
b) between about 10 to 30% of nonionic surfactants wherein about 7 to 10% is ethoxylated isotridecanol as a cleaning agent;
c) a thickening agent for giving said formulation a desired viscosity; and
d) water.

The present invention also provides a skin cleansing formulation, comprising:
a) between about 5% to about 10% by weight of at least one of a methylester of a saturated or unsaturated fatty acid;
b) between about 7 to 10% of a nonionic surfactant ethoxylated isotridecanol as a cleaning agent;
c) a thickening agent for giving said formulation a desired viscosity; and
d) water.

DETAILED DESCRIPTION OF THE INVENTION

A goal of the present invention is to provide a new heavy duty hand cleanser (HDHC), with or without solvent, with a high level of biodegradability and little or no ecotoxicity, with a high level of efficiency and a maximum skin tolerance and no systemic toxicity. The high level of potential biodegradability and low level of ecotoxicity potentially meet the criteria of the Scandinavian Swan label guidelines.

In the broadest aspect of the invention there is provided a cleansing formulation comprising 5 to 10% of one or more methylesters of vegetable saturated and/or unsaturated fatty acids which may be from several natural sources including sunflower seed oil, soybean oil, rape seed oil, or coconut oil. The formulation includes between about 10% to 30% of one or more surfactants and a preferred combination of surfactants includes at least one ethoxylated fatty alcohol, one alkyl polyoxyethylene glycol, one alkanolamide and one polymeric quaternary ammonium salt.

Preferred formulations include water present between about 10% to 80%, one or a combination of one or more scrubbing agents present in an amount between about 1% to about 10%. One or more viscosity-building agents are included to give the formulation the desired viscosity and these may include acrylic or acrylate polymers with or without mineral and/or a natural thickener. Cosmetic adjuvants may also be used in the formulation including preservatives, pigment, antioxydant, chelators and active substances including essential oils, essential fatty acids to mention just a few.

More particularly, preferred cleansing compositions include the following constituents:
1) Methyl ester of sunflower seed oil. This esterified vegetable oil contains essentially the two esters: methyl oleate and methyl linoleate. It has very good solvency properties on grease, is easily biodegradable, is not ecotoxic, is not toxic, is obtained from a renewable source and is not flammable. This ingredient is not used in any of the HDHC present on the market.
2) Ethoxylated isotridecanol. This cosmetic non ionic surfactant is readily biodegradable and is not an irritant. According to its average carbon chain length and its level of ethoxylation, its detergency power is theoretically very high. The combination of methyl ester of sunflower seed oil (5 to 10%) and ethoxylated isotridecanol (5 to 10%), at a total low concentration, gives the formulation the same level of cleansing efficiency as HDHC containing 20 to 30% of hydrocarbon solvent (results of lab tests) and also has a very good ecological profile. This combination does not exist on the market and the methyl ester of sunflower seed oil is not used alone either.

3) Tetradibutyl pentaerithrityl hydroxyhydrocinnamate. This antioxydant was recently launched by CIBA (Tinogard TTDD$^R$) and is thus not yet used in competitor HDHC. It is highly biodegradable, not ecotoxic and not toxic. It is used in the formulation to protect the methyl ester of sunflower seed oil from oxydation instead of using Butyl-Hydroxy-Anisol and/or Butyl-Hydroxy-Toluene commonly used in cosmetics and hygiene products.

4) Corn meal scrubber. This natural scrubbing agent is easily biodegradable, is is not ecotoxic, is not toxic and is obtained from a renewable source. It is very mild for the skin because it has no angle or rough surface and its hardness is sufficient to increase the cleansing efficiency by mechanical effect. The scrubbing agent may be of vegetable, mineral or plastic origins.

5) Essential oils of Mentha piperita, Mentha arvensis and Eucalyptus globulus. This combination of natural essential oils gives the product a pleasant fresh and flowery smell without perfume (perfumes are complex formulations containing 20 to 100 ingredients which are sometimes ecotoxic and/or irritant or sensitising).

6) The cleansing efficiency of the formulation is reinforced with one alkyl polyoxyethylene glycol (peg-33 castor oil) and one alkanolamide (cocamide dea) which both also have very good emolliency properties.

7) Emolliency is necessary to compensate the eventual defatting power of the preparation and to maintain the skin biomechanical and moisturising characteristics at an acceptable level. This emolliency level is reinforced with the use of polymeric quaternary ammonium salt (polyquaternium-7) whose chemical structure accounts for its affinity for the skin.

8) The formulation may include two cosmetic preservatives, dimethylol dimethyl hydantoin and dimethyl oxazolidine, give a synergistic association used to protect the preparation from the growth of microoganisms (Gram negative and Gram positive bacteria, yeast and molds).

9) One or more viscosity-building agents are preferably included in the cleansing formulation which have rheological properties which are useful for stabilising the emulsion and adjusting the final viscosity to the desired level. Examples of such agents include carbomer-like acrylic acid polymer with bentonite and/or xanthane gum with bentonite. Aminomethyl propanol is a cosmetic pH adjuster which may be included in the formulation. Titanium dioxide may be included in the formulation and is used as a cosmetic opacifier pigment.

EXAMPLE FORMULATIONS

Table 1 shows the chemicals and compositions used to produce the particular formulations shown in Tables 2 to 4.

TABLE 1

| CHEMICALS (INCI) | COMPOSITION |
| --- | --- |
| SUNFLOWER SEED OIL METHYL ESTER | METHYL OLEATE AND METHYL LINOLEATE |
| TRIDECETH-10 (ETHOXYLATED ISOTRIDECANOL) | POLYETHYLENE GLYCOL ETHER OF TRIDECYL ALCOHOL |
| COCAMIDE DEA | COCONUT DIETHANOLAMIDE |
| PEG-33 CASTOR OIL | POLYETHYLENE GLYCOL DERIVATIVE OF CASTOR OIL (Ricinus communis) |
| POLYQUATERNIUM-7 | POLYMERIC QUATERNARY AMMONIUM SALT CONSISTING OF ACRYLAMIDE AND DIMETHYL DIALLYL AMMONIUM CHLORIDE MONOMERS |
| CORN (ZEA MAYS) MEAL | CELLULOSE AND STARCH |
| ACRYLATES/C10-30 ALKYL ACRYLATE CROSSPOLYMER | COPOLYMER OF C10-30 ALKYL ACRYLATES AND ONE OR MORE MONOMERS OF ACRYLIC ACID |
| DIMETHYLOL DIMETHYL HYDANTOIN | 1,3-DIHYDROXYMETHYL-5,5-OL DIMETHYL HYDANTOIN |
| DIMETHYL OXAZOLIDINE | 4,4-DIMETHYL-1,3-OXAZOLIDINE |
| TETRADIBUTYL PENTAERITHRITYL HYDROXYHYDROCINNAMATE | TETRADIBUTYL PENTAERITHRITYL HYDROXY-HYDROCINNAMATE |
| AMINOMETHYLPROPANOL | AMINOMETHYLPROPANOL |
| TITANIUM DIOXYDE | TITANIUM DIOXYDE |
| ESSENTIAL OILS OF MENTHA PIPERITA/MENTHA ARVENSIS/ EUCALYPTUS GLOBULUS | ESSENTIAL OILS OF MENTHA PIPERITA/MENTHA ARVENSIS/ EUCALYPTUS GLOBULUS |
| BENTONITE | NATIVE HYDRATED COLLOIDAL ALUMINIUM SILICATE CLAY |
| XANTHANE GUM | HETEROPOLYSACCHARIDE GUM PRODUCED BY FERMENTATION OF A CARBOHYDRATE BY A BACTERIA (Xanthomonas campestris) |
| CARBOMER | HOMOPOLYMER OF ACRYLIC ACID CROSSLINKED WITH AN ALLYL ETHER OF PENTAERYTHRITOL |

The following are examples of cleansing formulations produced in accordance with the present invention Example 1

| INGREDIENTS | % wt |
| --- | --- |
| WATER | 73.64 |
| SUNFLOWER SEED OIL METHYL ESTER | 9.00 |
| TRIDECETH-10 (ETHOXYLATED ISOTRIDECANOL) | 7.00 |
| COCAMIDE DEA | 3.00 |
| PEG-33 CASTOR OIL | 2.00 |
| POLYQUATERNIUM-7 | 0.50 |
| CORN (ZEA MAYS) MEAL | 4.00 |
| ACRYLATES/C10-30 ALKYL ACRYLATE CROSSPOLYMER | 0.35 |
| DIMETHYLOL DIMETHYL HYDANTOIN | 0.10 |
| DIMETHYL OXAZOLIDINE | 0.10 |
| TETRADIBUTYL PENTAERITHRITYL HYDROXYHYDROCINNAMATE | 0.05 |
| AMINOMETHYLPROPANOL | 0.12 |
| TITANIUM DIOXYDE | 0.05 |
| ESSENTIAL OILS OF MENTHA PIPERITA/MENTHA ARVENSIS/EUCALYPTUS GLOBULUS | 0.09 |

Example 2

| INGREDIENTS | % wt |
| --- | --- |
| WATER | 60 to 80 |
| SUNFLOWER SEED OIL METHYL ESTER | 10.00 |
| TRIDECETH-10 (ETHOXYLATED ISOTRIDECANOL) | 10.00 |
| COCAMIDE DEA | 5.00 |
| PEG-33 CASTOR OIL | 2.00 |
| POLYQUATERNIUM-7 | 0.50 |
| CORN (ZEA MAYS) MEAL | 4.00 |
| CARBOMER | 0.20 |
| BENTONITE | 0.20 |
| DIMETHYLOL DIMETHYL HYDANTOIN | 0.10 |
| DIMETHYL OXAZOLIDINE | 0.10 |
| TETRADIBUTYL PENTAERITHRITYL HYDROXYHYDROCINNAMATE | 0.05 |
| AMINOMETHYLPROPANOL | 0.10 |
| TITANIUM DIOXYDE | 0.10 |
| ESSENTIAL OILS OF MENTHA PIPERITA/ MENTHA ARVENSIS/EUCALYPTUS GLOBULUS | 0.09 |

Example 3

| INGREDIENTS | % wt |
| --- | --- |
| WATER | 60 to 80 |
| SUNFLOWER SEED OIL METHYL ESTER | 10.00 |
| TRIDECETH-10 (ETHOXYLATED ISOTRIDECANOL) | 10.00 |
| COCAMIDE DEA | 5.00 |
| PEG-33 CASTOR OIL | 2.00 |
| POLYQUATERNIUM-7 | 0.50 |
| CORN (ZEA MAYS) MEAL | 4.00 |
| XANTHANE GUM | 0.50 |
| BENTONITE | 0.30 |
| DIMETHYLOL DIMETHYL HYDANTOIN | 0.10 |
| DIMETHYL OXAZOLIDINE | 0.10 |
| TETRADIBUTYL PENTAERITHRITYL HYDROXYHYDROCINNAMATE | 0.05 |
| AMINOMETHYLPROPANOL | 0.10 |
| TITANIUM DIOXYDE | 0.10 |
| ESSENTIAL OILS OF MENTHA PIPERITA/ MENTHA ARVENSIS/EUCALYPTUS GLOBULUS | 0.09 |

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A skin cleansing formulation, comprising:
   a) between about 5% to about 10% by weight of at least one of a methylester of a saturated or unsaturated fatty acid;
   b) between about 10 to 30% of nonionic surfactants wherein about 7 to 10% is ethoxylated isotridecanol as a cleaning agent;
   c) a thickening agent for giving said formulation a desired viscosity; and
   d) water.

2. The skin cleansing formulation according to claim 1 including between about 1 to about 10% of a scrubbing agent.

3. The skin cleansing formulation according to claim 1 wherein said at least one of a methylester of a saturated or unsaturated fatty acid is selected from the group consisting of sunflower seed oil, soybean oil, rape seed oil and coconut oil.

4. The skin cleansing formulation according to claim 2 wherein said scrubbing agent is one of a vegetable, or mineral or plastic origins.

5. The skin cleansing formulation according to claim 4 wherein said scrubbing agent is corn meal.

6. The skin cleansing formulation according to claim 1 including selected cosmetic adjuvants.

7. The skin cleansing formulation according to claim 1 wherein said thickening agent includes an acrylate copolymer.

8. The skin cleansing formulation according to claim 1 wherein said thickening agent is selected from the group consisting of xanthane gum, bentonite and combinations thereof.

9. The skin cleansing formulation according to claim 1 wherein said methylester of a saturated or unsaturated vegetable oil is methylester of sunflower seed oil.

10. The skin cleansing formulation according to claim 2 wherein said at least one of a methylester of a saturated or unsaturated fatty acid is selected from the group consisting of sunflower seed oil, soybean oil, rape seed oil and coconut oil.

11. The skin cleansing formulation according to claim 2, wherein said methylester of a saturated or unsaturated vegetable oil is methylester of sunflower seed oil.

12. The skin cleansing formulation according to claim 4, wherein said methylester of a saturated or unsaturated vegetable oil is methylester of sunflower seed oil.

13. The skin cleansing formulation according to claim 6, wherein said methylester of a saturated or unsaturated vegetable oil is methylester of sunflower seed oil.

14. The skin cleansing formulation according to claim 2 wherein said thickening agent includes an acrylate copolymer.

15. The skin cleansing formulation according to claim 3 wherein said thickening agent includes an acrylate copolymer.

16. A skin cleansing formulation, comprising:
   a) between about 5% to about 10% by weight of at least one of a methylester of a saturated or unsaturated fatty acid;
   b) between about 7 to 10% of a nonionic surfactant ethoxylated isotridecanol as a cleaning agent;
   c) a thickening agent for giving said formulation a desired viscosity; and
   d) water.

* * * * *